United States Patent [19]

Makino et al.

[11] Patent Number: 4,746,675
[45] Date of Patent: May 24, 1988

[54] EXTERNAL PHARMACEUTICAL COMPOSITION

[75] Inventors: Yuji Makino; Yoshiki Suzuki, both of Hino, Japan

[73] Assignee: Teijin Limited, Osaka, Japan

[21] Appl. No.: 924,189

[22] Filed: Oct. 27, 1986

Related U.S. Application Data

[63] Continuation of Ser. No. 595,835, Apr. 2, 1984, abandoned.

[30] Foreign Application Priority Data

Apr. 4, 1983 [JP]  Japan .................................. 58-57908

[51] Int. Cl.$^4$ ............................................. A61K 31/40
[52] U.S. Cl. .................................... 514/423; 514/946; 514/947
[58] Field of Search ........................ 514/423, 946, 947

[56] References Cited

PUBLICATIONS

Chem. Abst. 80:100119r, 1974.
Chem. Abst. 67:2026v, 1967.
R. Idson, J. Pharm. Sci. 64:919–921, 1975.

Primary Examiner—John Rollins
Attorney, Agent, or Firm—Wenderoth, Lind & Ponack

[57] ABSTRACT

A pharmaceutical composition for external use with the enhanced penetration of a pharmacologically active agent through the skin or mucosa of a warm-blooded animal, said composition comprising (A) a pharmaceutically effective amount of the pharmacologically active agent such as antiinflammatory agent, etc., and (B) a penetration enhancer of the following formula (1)

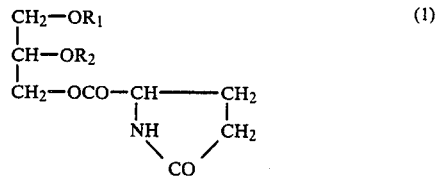

wherein $R_1$ and $R_2$ are identical or different and each represents H, a $C_{1-25}$ alkyl, $C_{2-25}$ alkenyl, a ($C_{1-24}$ alkyl)carbonyl or a ($C_{2-24}$ alkenyl)carbonyl, provided that $R_1$ and $R_2$ are not H at the same time, or $R_1$ and $R_2$, taken together, may form a group of the following formula (a)

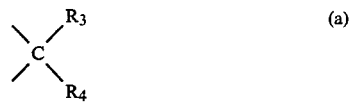

in which $R_3$ and $R_4$ are identical or different and each represents H, $C_{1-24}$ alkyl or $C_{1-24}$ alkenyl.

10 Claims, No Drawings

EXTERNAL PHARMACEUTICAL COMPOSITION

This application is a continuation, of now abandoned application Ser. No. 595,835, filed Apr. 2, 1984, now abandoned.

This invention relates to a pharmaceutical composition for external use. More specifically, it relates to a pharmaceutical composition for external use which enhances penetration of a pharmaceutically active agent through the skin or mucosa of a warmblooded animal.

Pharmacologically active agents can roughly be classified by the mode of administration into (1) those for internal use which are taken into the digestive tract through the oral cavity, (2) those to be injected into the body through an injection syringe, and (3) those for external use which are applied to the living body by methods other than the internal use and injection.

By the range within which their pharmacological action is expected, these pharmacologically active agents may be divided into those which are expected to exhibit a systemic action and those which are expected to exhibit a topical action.

For example, many of drugs for internal use are generally expected to show a systemic action or a selective action upon absorption through the digestive tract. They also include those drugs which are expected to show a topical action, such as anthelmintics, digestives and enteric antiseptics whose actions are relatively limited to the sites to which they have been applied.

Drugs for external use, on the other hand, are mostly expected to exhibit their action at local sites to which they have been applied.

The method of administration of a pharmacologically active agent is basically determined by considering by what administering method the pharmacological action of the pharmacologically active agent will be developed most effectively, and an undesirable physiological action which it more or less possesses can be most effectively inhibited.

For example, when a desirable pharmacological action possessed by a drug cannot be effectively developed by oral administration because of the decomposition of the drug in the digestive tract or its inability to pass through the membrane of the digestive tract but can be effectively developed by injection, it is better to administer the drug by injection than through the oral route. Furthermore, when a drug exhibits its desirable pharmacological action both by injection and by oral administration and does not undergo decomposition in the digestive tract nor is unable to pass through the membrane of the digestive tract, the oral route would generally be employed because of its ease of application. In the latter case, too, administration by injection would be preferred in an emergency case in which rapid development of the pharmacological action is expected.

Administration of drugs through the oral route or by injection has the aforesaid restrictions attributed to the drugs themselves, and by such an administration route, the concentrations of the drugs which are involved in in vivo reactions increases abruptly or relatively abruptly. Accordingly, where such an abrupt increase in concentration adversely affects the living body, administration through these routes should generally be avoided.

As stated above, drugs for external use are generally applied to expect their pharmacological actions at the site of application, presumably because the site at which the pharmacological action of a drug is desired to exhibited is the site of application of the drug or a site very near it. The external drugs have the advantage that their pharmacological actions are exhibited gradually over an extended period of time because they are gradually absorbed in the living body from the site of application. Accordingly, drugs which can develop their pharmacological activities upon absorption in the living body but which are not desired to increase abruptly in concentration in vivo because, for example, of the possibility of inducing an undesirable physiological action could be applied externally.

Most drugs which can exhibit their pharmacological activity only after absorption into the living body have the defect that when applied externally, they are not absorbed in sufficient concentrations through the skin or membrane. This is presumably because the drugs themselves cannot pass through the skin or membrane or can do so only very slowly, and before their concentrations reach effective ones in vivo they are metabolized.

It has previously been known to use sorption promotors, for example organic solvents such as dimethyl sulfoxide, dimethylacetamide and propylene glycol, organic esters such as diisopropyl adipate and isopropyl myristate, and surface-active agents such as sodium laurylsulfate and polyoxyethylene-20-sorbitan monolaurate, for enhancing penetration or permeation of the drugs through the skin or mucosa of the living body (see W. A. Ritschel, Angew. Chem. Internat. Edit., 1969, pp. 699–710).

U.S. Pat. No. 3,989,816 discloses that 1-substituted-azacycloheptan-2-ones represented by the following formula

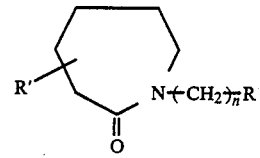

wherein R' is hydrogen or a lower alkyl group having 1 to 4 carbon atoms, R is a straight or branched chain alkyl group having 1 to 18 carbon atoms or an aryl group, and n is a positive integer of from 0 to 10, enhance the penetration of a physiologically active agent through the skin or membrane of a human or an animal.

U.S. Pat. No. 3,920,814 discloses that pyrrolidone-carboxylic acid represented by the following formula

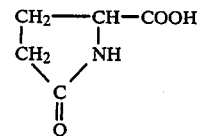

or a pharmaceutically acceptable derivative thereof is useful as a potentiating agent for antibiotics such as penicillins and cephalosporins and brings about a synergistic effect in that the activity of such an antibiotic and pyrroidone carboxylic acid used in combination is higher than the sum of the activities of these compounds used individually. The U.S. patent states that the aforesaid synergism (potentiation) has not yet been explained in terms of mechanism, and is quite silent upon whether or not the pyrrolidonecarboxylic acid or its derivative enhances the penetration of antibiotics through the skin or mucosa.

U.S. Pat. No. 3,836,665 discloses a topical dermatological composition containing a higher alkyl ester of 5-pyrrolidone-(2)-carboxylic acid of the formula

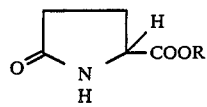

wherein R is a straight or branched chain alkyl group of 8 to 10 carbon atoms,
as an active ingredient.

It is an object of this invention to provide a pharmaceutical composition for external use comprising a compound which is novel as a penetration enhancer and has the action of enhancing the penetration of a pharmacologically active agent through the skin or mucosa of a warm-blooded animal.

Another object of this invention is to provide a pharmaceutical composition for external use comprising a pharmacologically active agent together with a compound being novel as a penetration enhancer and haviang the ability to enhance the penetration of the pharmacologically active agent through the skin or membrane of a warm-blooded animal when used externally.

Still another object of this invention is to cause a pharmacologically active agent being incapable of, or having difficulty in, penetrating the skin or membrane of a warm-blooded animal, for example a pharmacologically active agent having relatively high hydrophilicity or a relatively high molecular weight, to penetrate the skin or mucosa by using a compound having the above action and being novel as a penetration enhancer and to exhibit its desirable pharmacological activity.

Yet another object of this invention is to use a pharmacologically active agent, which when administered orally or by injection, is decomposed in the digestive tract, etc. or exhibits an undesirable physiological action, together with a compound having the aforesaid action and being novel as a penetration enhancer, and to develop the desirable activity of the pharmacologically active agent to an utmost extent while avoiding the aforesaid undesirable results.

A further object of this invention is to provide a pharmaceutical composition for external use comprising a pharmacologically active agent capable of exhibiting its pharmacological activity when externally used and a compound having the aforesaid action and being novel as a penetration enhancer, said composition being capable of developing a pharmacological activity equivalent to that of the pharmacologically active agent more rapidly or with a smaller amount of the pharmacologically active agent by the conjoint use of the penetration enhancer.

A still further object of this invention is to provide a pharmaceutical composition for external use comprising a pharmacologically active agent which tends to lose its activity by being metabolized in the liver and cannot maintain its minimum effective blood level over an extended period of time when internally administered and which when used together with a compound having the aforesaid activity and being novel as a penetration enhancer, maintains its minimum effective blood level over an extended period of time and effectively exhibits a systemic action. This composition is provided by utilizing the fact that unlike a pharmacologically active agent which is absorbed from the digestive tract and carried by the blood stream by internal administration, a pharmacologically active agent which is absorbed and carried by the blood stream by external administration returns to the heart before it passes through the liver and therefore takes a longer period of time until passage through the liver.

A yet further object of this invention is to provide a pharmaceutical composition for external use comprising a pharmacologically active agent which tends to lose its activity by being metabolized in the liver but which when applied externally together with a compound having the aforesaid activity and being novel as a penetration enhancer by utilizing the aforesaid blood stream in vivo, can be directly caused to act topically in an effective amount on a particular site at which it is desired to exhibit its pharmacological action.

An additional object of this invention is to provide a pharmaceutical composition for external use comprising a nontoxic and safe derivative of 1-pyroglutamyloxy-2,3-dihydroxypropane which is novel as a penetration enhancer, said composition being based on the present inventor's discovery that the above penetration enhancer compound enhances the penetration of a pharmacologically active agent when used together.

Other objects and advantages of this invention will become apparent from the following description.

In accordance with this invention, the aforesaid objects and advantages of the invention are achieved by a pharmaceutical composition for external use with the enhanced penetration of a pharmacologically active agent through the skin or mucosa of a warm-blooded animal, said composition comprising (A) a pharmaceutically effective amount of the pharmacologically active agent, and (B) a penetration enhancer of the following formula (1)

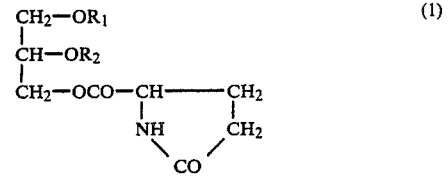

wherein $R_1$ and $R_2$ are identical or different and each represents a hydrogen atom, an alkyl group having 1 to 25 carbon atoms, and alkenyl group having 2 to 25 carbon atoms, a ($C_{1-24}$ alkyl)carbonyl group or a ($C_{2-24}$ alkenyl)carbonyl group, provided that $R_1$ and $R_2$ are not hydrogen atoms at the same time, or $R_1$ and $R_2$, taken together, may form a group of the following formula (a)

in which $R_3$ and $R_4$ are identical or different and each represents a hydrogen atom, an alkyl group having 1 to 24 carbon atoms or an alkenyl gorup having 2 to 24 carbon atoms.

The penetration enhancer used in this invention is the derivative of 1-pyroglutamyloxy-2,3-dihydroxypropane represented by the above formula (1) (to be referred to as a glycerol pyroglutamate).

In formula (1), $R_1$ and $R_2$ are identical or different and each represents a hydrogen atom, an alkyl group having 1 to 25 carbon atoms, an alkenyl group having 2 to 25 carbon atoms, a ($C_{1-24}$ alkyl)carbonyl group, or a ($C_{2-24}$ alkenyl)carbonyl group.

Examples of the alkyl groups with 1 to 25 carbon atoms include methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, eicosyl, docosyl, tricosyl, tetracosyl and pentacosyl groups. Examples of the alkenyl group having 2 to 25 carbon atoms include vinyl, allyl, geranyl, linalyl, neryl, phytyl, trans-2-butenyl, 2-hexenyl, 4-decenyl, 9-decenyl, 9-dodecenyl, 5-tetradecenyl, 9-tetradecenyl, 6-hexadecenyl, 9-hexadecenyl, 9-heptadecenyl, cis-8-octadecenyl, cis-9-octadecenyl, 9-eicosenyl, 11-docosenyl, 13-docosenyl, 15-tetracosenyl and 17-pentacosenyl groups.

Specific examples of $C_{1-24}$ alkyl and $C_{2-24}$ alkenyl in the ($C_{1-24}$ alkyl)carbonyl group and ($C_{2-24}$ alkenyl)carbonyl group will be apparent from the above exemplification.

These alkyl and alkenyl groups may be linear or branched.

Among these glycerol pyroglutamates, those of formula (1) in which $R_1$ is an alkyl group having 1 to 25 carbon atoms, an alkenyl group having 2 to 25 carbon atoms, a ($C_{1-24}$ alkyl)-carbonyl group or a ($C_{2-24}$ alkenyl)carbonyl group and $R_2$ is a hydrogen atom are preferred. Those in which $R_1$ is an alkyl group having 4 to 23 carbon atoms, an alkenyl group having 4 to 23 carbon atoms, a ($C_{4-22}$ alkyl)carbonyl group or a ($C_{4-22}$ alkenyl)-carbonyl group and $R_2$ is a hydrogen atom are especially preferred.

These preferred glycerol pyroglutamates are represented by the following formula (1)-1

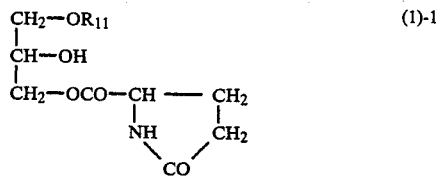

(1)-1 wherein $R_{11}$ represents an alkyl group having 1 to 25 carbon atoms, an alkenyl group having 2 to 25 carbon atoms, a ($C_{1-24}$ alkyl)carbonyl group or a ($C_{2-24}$ alkenyl)carbonyl group, preferably an alkyl group having 4 to 23 carbon atoms, an alkenyl group having 4 to 23 carbon atoms, a ($C_{4-22}$ alkyl)carbonyl group, or a ($C_{4-22}$ alkenyl)carbonyl group.

In formula (1), $R_1$ and $R_2$ may be taken together to form a group of the following formula (a)

(a)

wherein $R_3$ and $R_4$ are identical or different and each represents a hydrogen atom, a $C_{1-24}$ alkyl group or a $C_{2-24}$ alkenyl group.

Specific examples of the $C_{1-24}$ alkyl and $C_{2-24}$ alkenyl are apparent from the exemplification of $R_1$ and $R_2$ given above.

Specific examples of the group of formula (a) include mono($C_{1-24}$ alkyl)methylenes such as methylene, methylmethylene, ethylmethylene, propylmethylene, butylmethylene, pentylmethylene, hexylmethylene, octylmethylene, nonylmethylene, decylmethylene, dodecylmethylene, tetradecylmethylene, octadecylmethylene, eicosylmethylene and tricosylmethylene; di($C_{1-24}$ alkyl)methylenes such as dimethylmethylene, dipropylmethylene, dibutylmethylene, dihexylmethylene, didecylmethylene and dieicosylmethylene; mono($C_{2-24}$ alkenyl)methylenes such as vinylmethylene, propenylmethylene, butenylmethylene, pentenylmethylene, hexenylmethylene, octenylmethylene, nonenylmethylene, decenylmethylene, undecenylmethylene, dodecenylmethylene, eicosenylmethylene and tricosenylmethylene; di($C_{2-24}$ alkenyl)-methylenes such as divinylmethylene, dipropenylmethylene, dibutenylmethylene, dipentenylmethylene, dihexenylmethylene, dioctenylmethylene, dinonenylmethylene, didecenylmethylene, didodecenylmethylene, dieicosenylmethylene and ditricosenylmethylene; and mono($C_{1-24}$ alkyl)-mono($C_{2-24}$ alkenyl)methylenes such as methylvinylmethylene, propylvinylmethylene, and methylheptadecenylmethylene.

Of these glycerol pyroglutamates, those of the following formula (2)

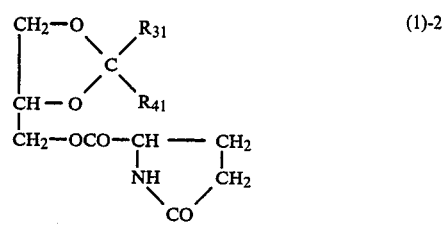

(1)-2 wherein $R_{31}$ and $R_{41}$ are identical or different and each represents a hydrogen atom, an alkyl group having 3 to 23 carbon atoms or an alkenyl group having 3 to 23 carbon atoms, provided that at least one of $R_{31}$ and $R_{41}$ is other than hydrogen, are especially preferred.

Specific examples of the glycerol pyroglutamates of formula (1) are given below.

Compounds of formula (1) in which at least one of $R_1$ and $R_2$ is an alkyl group having 1 to 25 carbon atoms or an alkenyl group having 2 to 25 carbon atoms (100) 2-Hydroxy-3-methoxy-1-pyroglutamyloxypropane, (102) 3-ethoxy-2-hydroxy-1-pyroglutamyloxypropane, (104) 3-hexyloxy-2-hydroxy-1-pyroglutamyloxypropane, (106) 2-hydroxy-3-octyloxy-1-pyroglutamyloxypropane, (108) 3-dodecyloxy-2-hydroxy-1-pyroglutamyloxypropane, (110) 2-hydroxy-3-pentadecyloxy-1-pyroglutamyloxypropane, (112) 2-hydroxy-3-octadecyloxy-1-pyroglutamyloxypropane, (114) 3-eicosyloxy-2-hydroxy-1-pyroglutamyloxy propane, (116) 2-hydroxy-3-tetracosyloxy-1-pyroglutamyloxypropane, (118) 2,3-dimethoxy-1-pyroglutamyloxypropane, (120) 2,3-diethoxy-1-pyroglutamyloxypropane,
(122) 2,3-dioctyloxy-1-pyroglutamyloxypropane,
(124) 2,3-dioctadecyloxy-1-pyroglutamyloxypropane,
(126) 2,3-dieicosyloxy-1-pyroglutamyloxypropane,
(128) 2-hydroxy-3-vinyloxy-1-pyroglutamyloxypropane,
(130) 3-allyloxy-2-hydroxy-1-pyroglutamyloxypropane,
(132) 3-(2-pentenyloxy)-2-hydroxy-1-pyroglutamyloxypropane,
(134) 3-(9-dodecenyloxy)-2-hydroxy-1-pyroglutamyloxypropane,
(136) 3-(9-eicosenyloxy)-2-hydroxy-1-pyroglutamyloxypropane
(138) 2,3-divinyloxy-1-pyroglutamyloxypropane,
(140) 2,3-di(2-pentenyloxy)-1-pyroglutamyloxypropane,
(142) 2,3-di(9-heptadecenyloxy)-1-pyroglutamyloxypropane,
(144) 2,3-di(9-eicosenyloxy)-1-pyroglutamyloxypropane, Compounds of formula (1) wherein at least one of $R_1$ and $R_2$ is a ($C_{1-24}$ alkyl)carbonyl group or a ($C_{2-24}$ alkenyl)carbonyl group (150) 3-acetyloxy-2-hydroxy-1-pyroglutamyloxypropane ($R_1$=acetyl, $R_2$=H),
(152) 2,3-diacetyloxy-1-pyroglutamyloxypropane ($R_1$ and $R_2$=acetyl),
(154) 2-hydroxy-3-propionyloxy-1-pyroglutamyloxypropane,
(156) 2-hydroxy-3-valeryloxy-1-pyroglutamyloxypropane,
(158) 2,3-divaleryloxy-1-pyroglutamyloxypropane,
(160) 2-hydroxy-3-octanoyloxy-1-pyroglutamyloxypropane,
(162) 2,3-dioctanoyloxy-1-pyroglutamyloxypropane,
(164) 2-hydroxy-3-palmitoyloxy-1-pyroglutamyloxypropane,
(166) 2-hydroxy-3-stearoyloxy-1-pyroglutamyloxypropane,
(168) 2-hydroxy-3-oleoyloxy-1-pyroglutamyloxypropane,
(170) 2,3,-dioleoyloxy-1-pyroglutamyloxypropane,
(172) 3-dodecanoyloxy-2-hydroxy-1-pyroglutamyloxypropane,
(173) 2-hydroxy-3-octadecanoyloxy-1-pyroglutamyloxypropane,
(174) 3-eicosanoyloxy-2-hydroxy-1-pyroglutamyloxypropane,
(176) 2-hydroxy-3-tricosanoyloxy-1-pyroglutamyloxypropane,
(178) 3-acryloyloxy-2-hydroxy-1-pyroglutamyloxypropane,
(180) 2,3-diacryloyloxy-1-pyroglutamyloxypropane,
(182) 2-hydroxy-3-methacryloyloxy-1-pyroglutamyloxypropane,
(184) 2-hydroxy-3(2-pentenoyloxy)-1-pyroglutamyloxypropane,
(186) 3-(9-dodecenoyloxy)-2-hydroxy-1-pyroglutamyloxypropane,
(188) 3-(9-eicosenoyloxy)-2-hydroxy-1-pyroglutamyloxypropane,
(190) 2,3-di(9-eicosenoyloxy)-1-pyroglutamyloxypropane,
(192) 3-(11-docosenoyloxy)-2-hydroxy-1-pyroglutamyloxypropane,
(194) 2-hydroxy-3-(9-tetradecenoyloxy)-1-pyroglutamyloxy Compounds of formula (1) wherein $R_1$ and $R_2$ together forms the group of formula (a)

(200) 2,3-dioxomethylene-1-pyroglutamyloxypropane ($R_3$, $R_4$=H),
(202) 2,3-dioxo-(dimethyl)methylene-1-pyroglutamyloxypropane ($R_3$, $R_4$=CH$_3$),
(204) 2,3-dioxo-(ethyl)methylene-1-pyroglutamyloxypropane, ($R_3$=H, $R_4$=CH$_2$CH$_3$),
(206) 2,3-dioxo-(dipropyl)methylene-1-pyroglutamyloxypropane,
(208) 2,3-dioxo-(hexyl)methylene-1-pyroglutamyloxypropane,
(210) 2,3-dioxo-(dihexyl)methylene-1-pyroglutamyloxypropane,
(212) 2,3-dioxo-(octyl)methylene-1-pyroglutamyloxypropane,
(214) 2,3-dioxo-(dioctyl)methylene-1-pyroglutamyloxypropane,
(216) 2,3-dioxo-(decyl)methylene-1-pyroglutamyloxypropane,
(218) 2,3-dioxo-(dodecyl)methylene-1-pyroglutamyloxypropane,
(220) 2,3-dioxo-(pentadecyl)methylene-1-pyroglutamyloxypropane,
(222) 2,3-dioxo-(heptadecyl)methylene-1-pyroglutamyloxypropane,
(224) 2,3-dioxo-(diheptadecyl)methylene-1-pyroglutamyloxypropane,
(226) 2,3-dioxo-(dieicosyl)methylene-1-pyroglutamyloxypropane,
(228) 2,3-dioxo-(vinyl)methylene-1-pyroglutamyloxypropane,
(230) 2,3-dioxo-(2-pentenyl)methylene-1-pyroglutamyloxypropane,
(232) 2,3-dioxo-(9-dodecenyl)methylene-1-pyroglutamyloxypropane,
(234) 2,3-dioxo-(9-heptadecenyl)methylene-1-pyroglutamyloxypropane,
(236) 2,3-dioxo-bis(9heptadecenyl)methylene-1-pyroglutamyloxypropane.

The glycerol pyroglutamates of formula (1) can be produced by methods known per se.

For example, a compound of formula (1) in which $R_1$ is alkyl, alkenyl or aliphatic acyl and $R_2$ is hydrogen can be produced by reacting an epihalohydrin such as epichlorohydrin with pyroglutamic acid to form a 3-halo-2-hydroxy-1-pyroglutamyloxypropane and then reacting the product with an alcoholate or a salt of an aliphatic carboxylic acid.

A compound of formula (1) in which $R_1$ is hydrogen and $R_2$ is alkyl, alkenyl or aliphatic acyl can be produced by first reacting a 2-halo-1,3-dihydroxypropane with a nearly stoichiometrical amount of an alcoholate or a salt (e.g. sodium salt of an aliphatic carboxylic acid to form a 2-(alkyloxy, alkenyloxy or aliphatic acyloxy)-1,3-dihydroxypropane, and then reacting (esterifying) the product with a nearly equimolar proportion of pyroglutamic acid.

A compound of formula (1) in which both $R_1$ and $R_2$ are alkyl, alkenyl or aliphatic acyl can be produced by subjecting a 2,3-dihalo-1-hydroxypropane and pyroglutamic acid to an esterification reaction to form a dihalo-1-pyroglutamyloxypropane, and thereafter reacting 1 mole of the resulting product with about 2 moles of an alcoholate or a salt (e.g., sodium salt) of an aliphatic carboxylic acid.

A compound of formula (1) in which $R_1$ and $R_2$ together form the group of formula (a) can be produced by subjecting 2,3-dihydroxy-1-pyroglutamyloxypropane and an aldehyde or ketone of the formula

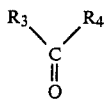

wherein $R_3$ and $R_4$ are as defined hereinabove, to a condensation reaction.

With regard to methods for producing the compounds of formula (1), Japanese Patent Publication No. 44773/1972 and Nippon Nogeikagaku Kaishi, Vol. 55, No. 10, pages 973–949 (1981) disclose a method of producing glycerin fatty acid pyroglutamic acid ester by reacting pyroglutamic acid or glutamic acid with a monoester of glycerin fatty acid under heat. This Japanese patent document describes that the glycerin fatty acid pyroglutamic acid ester obtained by the above method is effective as a surface-active agent for cosmetics or foodstuffs, an antistatic agent for plastics, and a softening agent for textile fibers. Japanese Patent Publication No. 2961/1974 states that pyroglutamic acid monoglyceride has a surface-activating action and is effective as an emulsifier, penetrant, detergent, softening agent, spreader or antistatic agent, and is considered to have a skin protecting action. Furthermore, Japanese Patent Publication No. 14776/1973 discloses that monoglyceride pyroglutamic acid esters are useful as antistatic agents for synthetic polymeric compounds.

The descriptions of these prior art documents cited above relating to glycerin fatty acid pyroglutamic acid esters, pyroglutamic acid monoglyceride and monoglyceride pyroglutamic acid esters and methods for their production are cited as part of the disclosure of the specification of the present application so long as these compoudns embrace part of the compounds of this invention represented by formula (1). These prior art documents, however, are quite silent on the fact that any of the compounds of formula (1) used in this invention has the property of enhancing the penetration of pharmacologically active agents.

The glycerol pyroglutamates of formula (1) in accordance with this invention are novel as a penetration enhancer which enhances the penetration of pharmacologically active agents through the skin or mucosa of a warm-blooded animal.

Since the pharmaceutical composition for external use in accordance with this invention comprising the glycerol pyroglutamate of formula (1) has a great ability to permit penetration of a pharmacologically active agent to penetrate the skin or mucosa, the present invention is applicable to pharmacologically active agents incapable of, or having difficulty in, penetrating the skin or mucosa, such as pharmacologically active agents having relatively high hydrophilicity or a relatively high molecular weight.

Furthermore, according to the composition of this invention, even those pharmacologically active agents which are known to penetrate the skin or mucosa can exhibit their pharmacological activities more rapidly after application, or can exhibit required pharmacological activity in smaller dosages.

When the composition of this invention is applied to pharmacologically active agents which are known to be unable to exhibit sufficient pharmacological activity in external use and have to be administered orally or by injection but which when administered orally or by injection, tend to undergo decomposition in the digestive tract, etc. or develop an undesirable physiological action, it is possible to have these agents exhibit sufficient pharmacological activities while circumventing the aforesaid undesirable results.

The composition of this invention is applicable therefore to a very large number of pharmacologically active agents including, for example, anti-inflammatory agents, agents for the circulatory system, antimicrobial agents, anti-ulcer agents, hormones, analgesic agents, anti-cancer agents, antiemetic agents, antiallergic agents, agents for the respiratory system, agents for the central nervous system, agents for the peripheral nervous system, biologicals and agents for the metabolic system.

More specific examples of the pharmacologically active agents that can be used in accordance with this invention are shown below.

The anti-inflammatory agents include, for example, nonsteroidal agents such as salicyclic acid, aspirin, acetoaminophene, aminopyrine, antipyrine, oxyphenbutazone, sulpyrine, indomethacin, sodium diclofenac, ibuprofen, slindac, naproxen, ketoprofen, etofenamate, salicylamide, salsalate, triethanolamine salicylate, apazone, fulfenamic acid, meclophenamic acid, demecolcine, allopurinol, oxypurinol, ibufenac, fenbufen, diflunisal, alcrofenac, phenylbutazone, mefenamic and, fenoprofen, bendazac, piroxicam and flurbiprofen; and steroidal agents such as amcinonide, prednisolone valerate acetate, diflucortolone valerate, betamethasone valerate, betamethasone acetate, dexamethazone acetate, betamethasone dipropionate, dexamethasone, triamcinolone acetonide, hydrocortisone, flumethasone pivalate, fluocinonide, fluocinolone acetonide, fluorometholone, fluodroxycortide, prednisolone, clobetasol propionate, beclometasone dipropionate, betametahsone, methylprednisolone, methylprednisolone acetate, and hydrocortisone butyrate.

The agents for the circulatory system include, for example, antihypertensive agents such as Rauwolfia alkaloids (e.g., reserpin and rescinnamine), clonidine, prazosin, dihydroergotamine mesylate, meticrane, methyldopa, guanethidine, betanidine and prostaglandins; vasodilators such as efloxate, etafenone, oxyfedrine, carbochromen, dilazep, diltiazem, trimetazidine, verapamil, pentaerythritol tetranitrate, dipyridamole, isosorbide dinitrate, trapidil, nitroglycerin, nifedipine, prenylamine, molsidomine, trotrolnitrate phosphate, inositol hexanicotinate, isoxsuprine, nylidrin, nicamate citrate, cyclandelate, cinnarizine, nicotinic alcohol and hepronicate; antiarrhythmic agents such as acebutolol, alprenolol, indenolol, oxprenolol, carteolol, bucumolol, bufetolol, bupranolol, propranolol and pindolol; and anticoagulants such as heparin, chondroitin sulfate and prostaglandins.

The antimicrobial agents include, for example, penicillin-type antibiotics such as penicillin G, penicillin V, methicillin, oxacillin, cloxacillin, ampicillin, hetacillin, cyclacillin, amoxycillin, carbenicillin and sulbenicillin; cepharosporin-type antibiotics such as cephaloridin, cephalothin, cephazolin, cephaloglycin and cephalexin; aminoglycoside-type antibiotics such as streptomycin, kanamycin, dibekacin, gentamicin and fradiomycin; tetracycline-type antibiotics such as oxytetracycline, tetracycline, dimethylchlorotetracycline, doxycycline and minocycline; macrolide-type antibiotics such as erythromycin, leucomycin, josamycin and spiramycin;

lincomycin-type antibiotics such as lincomycin and clindamycin; other antibiotics such as chloramphenicol, novobiocin, micamycin, bacitracin, gramicidin, gramicidin S, viomycin, capreomycin, cycloserin, enviomycin, rifampicin, nystatin, pentamycin, trichomycin, amphotericin B, griseofulvin, variotin, pyrrolnitrin, nitrofurantoin, thiabendazole, cephamycin, phosphonomycin, N-formidoylthienamycin monohydrate, and 1-ethyl-6-fluoro-1,4-dihydro-4-oxo-7-(1-piperazinyl)-3-quinolinecarboxylic acid; external sulfur drugs such as acetyl mafenide, sulfadiazine, silver sulfadiazine, sodium sulfamethoxazal, sulfisomidine, and sodium sulfisomidine; and other drugs such as iodine, povidoneiodine, diiodohydrooxyquine, benzalkonium chloride, benzethonium chloride, methylrosaniline chloride, hexachlorophene, chlorohexidine hydrochloride, benzoyl peroxide, tolunaftate, and 5-iodo-2'-deoxyuridine.

The anti-ulcer agents include, for example, prostaglandins such as 17,20-dimethyl-6-oxoprostaglandin $E_1$ methyl ester, 15-methyl-prostaglandin $E_2$, 16-methyl-16-hydroxy-15-dehydroxyprostaglandin $E_1$ methyl ester, 7-thiaprostaglandin $E_1$ methyl ester, and 17,20-dimethyl-7-thiaprostaglandin $E_1$ methyl ester.

The hormones include, for example, insulin, angiotensin, varopressin, felylpressin, protirelin, gonadotropin-releasing hormone, corticotropin, prolactin, somatotropin, thyrotropin, luteinizing hormone, calcitonin, kallikrein, parathyrin, glucagon, oxytocin, gastrin, secretin, serum gonadotropin, and sex hormones such as estrogen, estradiol, testosterone, and progesterone.

The analgesic agents include, for example, azapropazone, benzydamine, plenacetin, butylon, mepirizole, triaromide and migrenin.

The anticancer agents include, for example, 5-fluorouracil, 6-mercaptopurine, mycophenolic acid, methotrexate, bleomycin, mitomycin C, carbazilquinone, actinomycin C, carzinophlin, daunorubicin, doxorubicin, neocarzinostatin, chromomycin $A_3$, L-asparaginase, picibanil, podophyllotoxin, vinblastine and vincristine.

Examples of the antiemetic agents include pipamazine, chlorpromazine and dimenhydrinate.

Examples of the antiallergic agents are cycloheptadine hydrochloride and cinnarizine.

Antiasthma agents such as disodium cromoglycate may be cited as examples of the agents for the respiratory system.

Examples of the agents for the central nervous system include diazepams such as flurazepam, nimetazepam, nitrazepam and estazolam, and scoposamin.

The agents for the peripheral nervous system include, for example, benzocain, procaine, propoxycaine, dibucanine, lidocanine, mepivacaine, bupivacaine and tetracaine.

The biologicals include, for example, enzymes such as trypsin, papain, protease, lysozyme, streptokinase, plasmin, urokinase, hyaluronidase, α-chymotrypsin, serratiopeptidase, bromelain, and seaprose; microbial cell extracts such as PSK; inferferon; and interleukin.

The agents for the metabolic system include, for example, fat-soluble vitamins such as 1,25-dihydroxyvitamin $D_3$, 1α-hydroxyvitamin $D_3$, 1,24-dihydroxyvitamin $D_3$, 24,25-dihydroxyvitamin $D_3$, 1α, 25-dihydroxyvitamin $D_3$-26, 23-lactone, and 25-hydroxyvitamin $D_3$-26, 23-lactone.

It should be understood that the above-cited drugs are only some examples of phamacologically active agents which can be applied to the composition of this invention, because almost all drugs do not penetrate, or have difficulty in penetrating, the skin or mucosa.

Among the above-cited drugs, salicyclic acid, nitroglycerin, isosorbide dinitrate, pentaerythritol tetranitrate, testosterone, progesteron, estrogen estradiol, and scoporamin are known to be absorbed through the skin or mucosa. According to the present invention, the penetration of even these drugs can be enhanced. Hence, their pharmacological activity can be developed more rapidly after application, and the amount of these drugs to be applied can be decreased.

Furthermore, those drugs which have previously been administered orally but with undesirable side-effects such as a great tendency to induce ulcer formation on the gastric wall, for example anti-inflammatory agents such as indomethacin, salicyclic acid, aspirin and phenylbutazone or anticancer agents such as 5-fluorouracil and 6-mercaptopurine can effectively develop their desirable pharmacological activities with inhibited side-effects if applied to the skin or mucosa as the pharmaceutical composition of this invention.

Furthermore, those drugs which have previously been administered orally but with susceptibility to decomposition in the digestive tract or to metabolization and have had difficulty in developing their pharmacological activities sufficiently, for example nitroglycerin, isosorbide dinitrate, nifedipine, acebutorol, alprenolol, propranolol, insulin, testosterone, alcitonin, prostaglandins, interferon and interleukin can exhibit their pharmacological activities sufficiently while inhibiting their decomposition or metabolization when applied to the skin or mucosa as the pharmaceutical composition of this invention. Since the penetration enhancer of formula (1) in accordance with this invention enhances the penetration of a drug from the skin or mucosa, it can inhibit the decomposition of the drug in the digestive tract to the greatest possible extent, and also prolong the time which elapses until the drug is metabolized in the liver, thus maintaining the minimum effective level in the blood over an extended period of time.

Among the above-exemplified drugs, cepharosporin-type antibiotics such as cephaloridin, cephalothin and cephazolin and penicillin-type antibiotics such as carbenicillin and sulbenicillin have not been able to penetrate the skin or mucosa because of their especially high molecular weights or high hydrophilicity. By formulating such antibiotics into pharmaceutical compositions for external application in accordance with this invention, these drugs can penetrate the skin or mucosa to an extent that their pharmaceutical activities can be effectively exhibited.

The above and other advantages of the pharmaceutical compositions for external use in accordance with this invention will become apparent from the following Examples.

The term "external" or "externally", as used in the present specification and the appended claims, expresses the application of a drug or a composition containing it to the skin of a warm-blooded animal or the mucosa of a specified site of a warm-blooded animal such as the mucosa of the oral cavity, the mucosa of the nasal cavity, the mucosa of the rectum or the mucosa of the vagina. Accordingly, the term "external" or "externally" is used irrespective of whether the pharmacological action of a drug in the composition of this invention is developed topically or systemically. As will be clear from the specific examples of the drugs given hereinabove and their descriptions, the compositions of this invention include not only those which develop a topical action but also those which develop a systemic action.

The composition of this invention may comprise an ordinary pharmaceutically acceptable carrier or adjuvant in addition to the pharmacologically active agent and the penetration enhancer of formula (1).

The pharmaceutical composition of this invention may be in the form of a solution, a suspension, a semisolid, a powder, a solid of a fixed shape such as a tablet, or a film depending upon the pharmaceutically acceptable carrier or adjuvant. Accordingly, the composition of this invention can be prepared into a suitable form depending upon the site of application, etc.

The forms of the composition of this invention may be classified as shown below according to the classification in the art. The composition in the form of a solution includes solutions, aerosols, and capsules having a gelatin shell. The composition in the form of a suspension includes suspensions, lotions, aerosols, and capsules having a gelatin shell. The semisolid composition includes ointments, creams, liminents, pastes and gels. The powdery composition includes powders, capsules and granules. The composition to be molded into a definite shape includes tablets, and body temperature soluble solid preparations. The composition in the form of a film includes plasters, tapes and films.

The pharmaceutically acceptable carrier or adjuvants used in the composition of this invention is known to the art. Suitable carriers or adjuvants may be used depending upon the desired form of the composition. For example, beeswax, vegetable oils, lanolin, boric acid and white Vaseline are used for ointments. Oils and fats, waxes, higher fatty acids, higher alcohols, etc. are used for creams. Ethanol, glycerol, butylene glycol etc. are used for lotions. Tragacanth, gum arabic, sodium alginate, gelatin, methyl cellulose, CMC, etc. are usually used for suspensions. For body temperature soluble solid preparations, Vaseline, oils and fats such as cacao butter, palm oil, coconut oil, or fractionated coconut oil, etc. are normally used. Methyl cellulose, hydroxypropyl cellulose, hydroxypropyl methyl cellulose, crystalline cellulose, starch, etc. are used for tablets and granules. For films, hydroxypropyl cellulose, methyl cellulose, polyvinyl pyrrolidone, polyvinyl alcohol, etc. may be used.

The composition of this invention comprising such a carrier or adjuvant may be produced by known methods usually practiced in the art.

The composition of this invention should contain a pharmaceutically effective amount of the pharmacologically active agent. The amount varies naturally with the type of the pharmaceutically active agent, and also with the form of the composition of this invention or the site of its application. The dosages previously known of the drugs mentioned above are an effective tentative measure for determining the effective amount of a given drug. The composition of this invention may contain the drugs in amounts smaller or larger than the previously known dosages. For example, it can contain a drug in an amount 0.3 to 5 times the dosage previously known.

Generally, when a drug is applied to the skin as an external agent, not all of the drug contained in the external agent penetrates into the body through the skin. In view of this, it is surprising to note that according to the composition of this invention, even those drugs which have heretofore been administered orally or by injection can sufficiently exhibit their expected effects by using them in amounts which are do not greatly differ from the known dosages.

For example, when the composition of this invention containing isosorbide known as a vasodilator in the same amount as the usual dosage (oral) per administration is formed into a tape (10 cm × 10 cm) and applied to the skin, the expected effect can be exhibited sufficiently.

The composition of this invention contains the penetration enhancer of formula (1) in an amount of 0.2 to 25% by weight, preferably 0.5 to 15% by weight, based on the total weight of the composition.

It will be seen from the foregoing that the present invention also provides a method of administering a pharmacologically active agent to a warm-blooded animal, which comprises externally applying (A) a pharmaceutically effective amount of the pharmacologically active agent in combination with (B) a penetration enhancer of the above formula (1) to the surface of the skin or mucosa of the warm-blooded animal to enhance the penetration of the pharmacologically active agent through the skin or mucosa.

The mucosa mentioned above may be that of the rectum, oral cavity, nasal cavity or vagina of the warm-blooded animal.

In accordance with the method of this invention, the pharmacologically active agent may be applied to one or several sites of the skin or mucosa, and once or several times a day.

Preferably, the pharmacologically active agent is applied to the skin or mucosa as the pharmaceutical composition for external use in accordance with this invention.

The following Examples illustrate the present invention more specifically.

EXAMPLE 1

An ointment was prepared from 1 part by weight of indomethacin, 10 parts by weight of compound (168) and 89 parts by weight of a hydrophilic ointment (composed of 250 parts of white Vaseline, 220 parts by weight of stearyl alcohol, 120 parts by weight of propylene glycol, 15 parts by weight of sodium laurylsulfate, 0.25 part by weight of ethyl p-hydroxybenzoate, 0.15 part by weight of propyl p-hydroxybenzoate and a small amount of purified water). The back of a rat (body weight about 250 g) was cut by an electric hair-clipper, and 100 mg of the resulting ointment was applied by a finger to a circular unhaired portion, 4 cm in diameter. The blood was drawn from the tail of the rat periodically, and the concentration of indomethacin in the blood was determined periodically by high-performance liquid chromatography.

For comparison, the same ointment as above except that pyroglutamic acid was added instead of compound (168), the same ointment as above except that monooleyl glycerin ester was used instead of compound (168), and an ointment composed of 1 part by weight of indomethacin and 99 parts of by weight of the hydrophilic ointment were used, and the blood levels of indomethacin were measured in the same way as above after applying them to the backs of rats.

The results obtained are shown in Table 1. It is seen that the absorption of indomethacin from the ointment containing compound (168) (the composition of this invention) is better than the comparative ointments. In all of the above runs, changes such as erythema on the skin to which the drug compositions were applied were not observed.

After the final drawing of the blood, the rats were killed and the stomach was extracted and incised inwardly for the formation of an ulcer. In all of the above runs, no formation of an ulcer in the stomach was noted.

TABLE 1

| Ointment composition (wt. %) | | Concentration of indomethacin in the blood (μg/ml) | | | | |
|---|---|---|---|---|---|---|
| | | 1 hr | 3 hrs | 5 hrs | 7 hrs | 24 hrs |
| Example 1 | Indomethacin | 1 | 1.5 | 4.5 | 4.6 | 4.5 | 1.2 |
| | Compound (168) | 10 | | | | | |
| | Hydrophilic ointment | 89 | | | | | |
| Comparison 1 | Indomethacin | 1 | 1.4 | 2.2 | 2.0 | 1.8 | 0.7 |
| | Pyroglutamic acid | 10 | | | | | |
| | Hydrophilic ointment | 89 | | | | | |
| Comparison 2 | Indomethacin | 1 | 0.1 | 0.3 | 0.5 | 0.5 | 0.4 |
| | Hydrophilic ointment | 99 | | | | | |
| Comparison 3 | Indomethacin | 1 | 1.4 | 2.1 | 1.9 | 1.8 | 0.6 |
| | Monooleyl glycerin ester | 10 | | | | | |
| | Hydrophilic ointment | 89 | | | | | |

EXAMPLES 2 TO 20

Various ointments were prepared from 1 part by weight of indomethacin, 10 parts of each of various penetration enhancers shown in Table 2 and the hydrophilic ointment, and tested as in Example 1. For comparison, an ointment composed of 1 part by weight of indomethacin and 99 parts by weight of the hydrophilic ointment without the penetration enhancer was tested in the same way as above. The results are shown in Table 2.

In all of these runs, changes such as erythema were noted on the skin to which the drugs were administered.

No ulcer formation was observed in the stomach in these runs.

TABLE 2

| | Penetration enhancer | Concentration of indomethacin in the blood | | | | |
|---|---|---|---|---|---|---|
| | | 1 hr. | 3 hrs. | 5 hrs. | 7 hrs. | 24 hrs. |
| Example 2 | Compound (156) | 0.9 | 2.9 | 3.4 | 3.5 | 1.0 |
| Example 3 | Compound (160) | 1.5 | 4.0 | 3.1 | 3.1 | 0.7 |
| Example 4 | Compound (172) | 1.2 | 3.3 | 3.5 | 3.6 | 1.8 |
| Example 5 | Compound (173) | 1.1 | 3.1 | 3.6 | 3.5 | 1.1 |
| Example 6 | Compound (158) | 1.4 | 4.1 | 2.9 | 2.9 | 1.2 |
| Example 7 | Compound (162) | 1.5 | 3.4 | 3.8 | 3.7 | 1.6 |
| Example 8 | Compound (184) | 1.2 | 3.6 | 4.0 | 3.8 | 1.2 |
| Example 9 | Compound (192) | 0.9 | 3.5 | 3.3 | 3.5 | 1.3 |
| Example 10 | Compound (170) | 1.1 | 3.2 | 3.1 | 3.6 | 1.0 |
| Example 11 | Compound (104) | 1.3 | 3.5 | 3.6 | 3.3 | 1.6 |
| Example 12 | Compound (108) | 1.3 | 3.8 | 3.3 | 3.1 | 1.4 |
| Example 13 | Compound (112) | 0.8 | 3.4 | 3.4 | 3.4 | 1.3 |
| Example 14 | Compound (122) | 1.2 | 3.4 | 3.2 | 3.3 | 1.5 |
| Example 15 | Compound (124) | 0.9 | 3.6 | 3.5 | 2.8 | 0.7 |
| Example 16 | Compound (134) | 1.3 | 3.3 | 3.4 | 3.5 | 1.0 |
| Example 17 | Compound (142) | 1.4 | 3.7 | 4.2 | 3.4 | 1.2 |
| Example 18 | Compound (202) | 1.2 | 3.1 | 3.6 | 3.6 | 0.9 |
| Example 19 | Compound (214) | 1.3 | 3.6 | 3.3 | 3.3 | 2.1 |
| Example 20 | Compound (220) | 0.8 | 2.9 | 3.7 | 3.3 | 1.7 |
| Comparison 5 | None | 0.1 | 0.3 | 0.5 | 0.5 | 0.4 |

EXAMPLES 21 AND 22

An ointment was prepared from 1 part by weight of salicyclic acid, 10 parts by weight of compound (168) or compound (173) and 89 parts by weight of the hydrophilic ointment, and tested in the same way as in Example 1. For comparison, an ointment composed of 1 part by weight of salicyclic acid and 99 parts by weight of the hydrophilic ointment without the penetration enhancer was prepared, and tested in the same way as in Example 1.

The results are shown in Table 3.

TABLE 3

| Ointment composition (% by weight) | | Concentration of salicyclic acid in blood (μg/ml) | | | | |
|---|---|---|---|---|---|---|
| | | 1 hr | 3 hrs | 5 hrs | 7 hrs | 24 hrs |
| Example 21 | Salicyclic acid | 1 | 1.4 | 3.8 | 4.9 | 4.8 | 1.3 |
| | Compound (168) | 10 | | | | | |
| | Hydrophilic ointment | 89 | | | | | |
| Example 22 | Salicyclic acid | 1 | 1.5 | 4.0 | 5.0 | 4.3 | 0.9 |
| | Compound (173) | 10 | | | | | |
| | Hydrophilic ointment | 89 | | | | | |
| Comparison 6 | Salicyclic acid | 1 | 0.2 | 0.7 | 0.6 | 0.6 | 0.3 |
| | Hydrophilic ointment | 99 | | | | | |

EXAMPLE 23

An ointment was prepared from 0.15 part by weight of betamethasone valerate, 9.85 parts by weight of compound (168) and 90 parts by weight of the hydrophilic ointment.

In accordance with the method of R. Passarella et al. [Argneim. Forsch 30, (I), Nr. 4, 647–651 (1980)], the carrageenan edema inhibiting effect of the above ointment was examined. Specifically, 0.1 ml of a 1% carrageenan suspension in 0.9% NaCl solution was injected into the tip of the right leg of a rat (body weight 150–175 g). The foot volume was measured immediately after administration of carrageenan and 3, 5, and 6 hours after the administration by means of a mercury displacement device. 0.5, 1 and 2 hours after the administration of carrageenan, 100 mg of the ointment was well bubbled into each of the sites which underwent inflammation.

For comparison, an ointment composed of 0.15 part by weight of betamethasone valerate and 99.85 parts by weight of the hydrophilic ointment without including the compound (168) and the hydrophilic ointments were prepared and tested in the same way as above.

The percentage inhibitions were calculated on the basis of the percentage increase in foot volume of a rat to which only the hydrophilic ointment was administered, and the results are shown in Table 4.

TABLE 4

| | Ointment composition (% by weight) | | Percentage inhibition based on the control (%) | | |
|---|---|---|---|---|---|
| | | | 3 hrs | 5 hrs | 6 hrs |
| Example 23 | Betamethasone valerate | 0.15 | 19.7 | 36.8 | 39.2 |
| | Compound (168) | 9.85 | | | |
| | Hydrophilic ointment | 90 | | | |
| Comparison 7 | Betamethasone valerate | 0.15 | 9.1 | 10.3 | 15.0 |
| | Hydrophilic ointment | 99.85 | | | |

EXAMPLES 24 TO 42

Various ointments were prepared from 0.15 part by weight of betamethasone valerate, 19 parts by weight of the various penetration enhancers shown in Table 5, and 85 parts by weight of the hydrophilic ointment, and tested in the same way as in Example 23. For comparison, an ointment composed of 0.15 part by weight of betamethasone valerate and 99.85 parts by weight of the hydrophilic ointment, and the hydrophilic ointment alone were tested in the same way as above.

The results are shown in Table 5.

TABLE 5

| | Penetration enhancer | Percentage inhibition vs. control (%) | | |
|---|---|---|---|---|
| | | 3 hrs. | 5 hrs. | 6 hrs. |
| Example 24 | Compound (156) | 18.6 | 35.1 | 34.3 |
| Example 25 | Compound (160) | 17.7 | 30.8 | 29.9 |
| Example 26 | Compound (172) | 18.1 | 37.2 | 35.5 |
| Example 27 | Compound (173) | 15.3 | 32.3 | 33.4 |
| Example 28 | Compound (158) | 18.0 | 36.0 | 36.1 |
| Example 29 | Compound (162) | 16.1 | 34.0 | 34.2 |
| Example 30 | Compound (184) | 19.0 | 35.3 | 35.5 |
| Example 31 | Compound (192) | 19.5 | 36.7 | 30.8 |
| Example 32 | Compound (170) | 17.9 | 33.4 | 36.2 |
| Example 33 | Compound (104) | 18.3 | 35.3 | 37.0 |
| Example 34 | Compound (108) | 20.1 | 36.7 | 36.7 |
| Example 35 | Compound (112) | 17.8 | 32.2 | 33.0 |
| Example 36 | Compound (122) | 20.2 | 36.5 | 38.3 |
| Example 37 | Compound (124) | 19.5 | 37.8 | 36.6 |
| Example 38 | Compound (134) | 16.4 | 30.3 | 34.2 |
| Example 39 | Compound (142) | 16.5 | 34.6 | 34.0 |
| Example 40 | Compound (202) | 17.7 | 39.6 | 36.1 |
| Example 41 | Compound (214) | 18.2 | 35.3 | 35.5 |
| Example 42 | Compound (220) | 16.6 | 29.7 | 29.8 |

TABLE 5-continued

| | Penetration enhancer | Percentage inhibition vs. control (%) | | |
|---|---|---|---|---|
| | | 3 hrs. | 5 hrs. | 6 hrs. |
| Comparison 8 | None | 9.1 | 10.3 | 15.0 |

EXAMPLE 43

An ointment composed of 1 part by weight of nifedipine, 10 parts by weight of compound (168) and 89 parts by weight of the hydrophilic ointment was prepared. The back of a rat (body weight about 250 g) was cut by an electrical hair-clipper. 100 mg of the ointment was rubbed into a circular unhaired portion, 4 cm in diameter. Blood was drawn from the tail portion of the rat periodically, and the concentration of nifedipine in the blood was periodically determined by gas chromatography (electron capture-type detector).

For comparison, an ointment of the same formulation as above except that diisopropyl adipate was used instead of compound (168), and an ointment composed of 1 part of nifedipine and 99 parts by weight of the hydrophilic ointment without the inclusion of compound (168) were prepared, and tested in the same way as above.

The results are given in Table 6.

TABLE 6

| | Ointment composition (wt. %) | | Concentration of nifedipine in blood (ng/ml) | | | | |
|---|---|---|---|---|---|---|---|
| | | | 1 hr | 3 hrs | 5 hrs | 7 hrs | 24 hrs |
| Example 43 | Nifedipine | 1 | 12 | 19 | 31 | 25 | 24 |
| | Compound (168) | 10 | | | | | |
| | Hydrophilic ointment | 89 | | | | | |
| Comparison 9 | Nifedipine | 1 | 7 | 15 | 16 | 13 | 9 |
| | Diisopropyl adipate | 10 | | | | | |
| | Hydrophilic ointment | 89 | | | | | |
| Comparison | Nifedipine | 1 | 4 | 11 | 9 | 8 | 5 |
| | Hydrophilic ointment | 99 | | | | | |

EXAMPLES 44 TO 62

Various ointments were prepared from 1 part by weight of nifedipine, 10 parts by weight of the various penetration enhancers shown in Table 7 and 89 parts by weight of the hydrophilic ointment were prepared, and tested in the same way as in Example 43.

For comparison, an ointment composed of 1 part by weight of nifedipine and 91 parts by weight of the hydrophilic ointment without the inclusion of the penetration enhancer was tested in the same way as above.

The results are shown in Table 7.

TABLE 7

| | Penetration enhancer | Concentration of nifedipine in the blood (mg/ml) | | | | |
|---|---|---|---|---|---|---|
| | | 1 hr. | 3 hrs. | 5 hrs. | 7 hrs. | 24 hrs. |
| Example 44 | Compound (156) | 13 | 17 | 35 | 30 | 19 |
| Example 45 | Compound (160) | 18 | 21 | 41 | 25 | 20 |
| Example 46 | Compound (172) | 12 | 19 | 39 | 29 | 19 |
| Example 47 | Compound (173) | 16 | 18 | 34 | 27 | 26 |
| Example 48 | Compound (158) | 19 | 20 | 40 | 26 | 24 |
| Example 49 | Compound (162) | 17 | 18 | 36 | 28 | 20 |
| Example 50 | Compound (184) | 15 | 19 | 30 | 24 | 23 |
| Example 51 | Compound (192) | 14 | 20 | 34 | 27 | 22 |
| Example 52 | Compound (170) | 17 | 20 | 33 | 28 | 21 |

TABLE 7-continued

| | Penetration enhancer | Concentration of nifedipine in the blood (mg/ml) | | | | |
|---|---|---|---|---|---|---|
| | | 1 hr. | 3 hrs. | 5 hrs. | 7 hrs. | 24 hrs. |
| Example 53 | Compound (104) | 18 | 19 | 39 | 24 | 22 |
| Example 54 | Compound (108) | 14 | 17 | 41 | 28 | 21 |
| Example 55 | Compound (112) | 17 | 19 | 33 | 25 | 24 |
| Example 56 | Compound (122) | 16 | 18 | 36 | 27 | 26 |
| Example 57 | Compound (124) | 15 | 21 | 26 | 29 | 22 |
| Example 58 | Compound (134) | 15 | 19 | 38 | 25 | 23 |
| Example 59 | Compound (142) | 16 | 20 | 38 | 27 | 22 |
| Example 60 | Compound (202) | 18 | 18 | 35 | 26 | 24 |
| Example 61 | Compound (214) | 14 | 22 | 40 | 31 | 23 |
| Example 62 | Compound (220) | 10 | 23 | 38 | 29 | 25 |
| Comparison 11 | None | 4 | 11 | 9 | 8 | 5 |

EXAMPLE 63

An ointment composed of 5 parts by weight of isosorbide dinitrate, 10 parts by weight of compound (168) and 85 parts by weight of the hydrophilic ointment was prepared. The back of a rat (body weight about 250 g) was cut by an electrical hair-clipper, and 100 mg of the ointment was rubbed into a circular unhaired portion, diameter 4 cm, by a finger. The blood was drawn from the tail portion of the rat periodically, and the concentration of isosorbide dinitrate in the blood was determined periodically by gas chromatography (electron capture-type detector).

For comparison, the same ointment as above except that it contained diisopropyl adipate instead of compound (168), and an ointment composed of 5 parts by weight of isosorbide dinitrate and 95 parts of the hydrophilic ointment without the inclusion of the compound (168) were tested in prepared and tested in the same way as above.

The results are shown in Table 8.

TABLE 8

| Ointment composition (wt. %) | | | concentration of isosorbide dinitrate in blood (ng/ml) | | | | |
|---|---|---|---|---|---|---|---|
| | | | 1 hr | 3 hrs | 5 hrs | 7 hrs | 24 hrs |
| Example 63 | isosorbide dinitrate | 5 | 0.8 | 1.9 | 3.1 | 2.7 | 2.0 |
| | Compound (168) | 10 | | | | | |
| | Hydrophilic ointment | 85 | | | | | |
| Comparison 12 | isosorbide dinitrate | 5 | 0.4 | 1.1 | 1.2 | 0.9 | 0.9 |
| | Diisopropyl | 10 | | | | | |
| | Hydrophilic ointment | 65 | | | | | |
| Comparison 13 | isosorbide dinitrate | 5 | 0.4 | 0.7 | 0.5 | 0.8 | 0.6 |
| | Hydrophilic ointment | 95 | | | | | |

EXAMPLES 64 TO 82

Various ointments were prepared from 5 parts by weight of isosorbide dinitrate, 10 parts by weight of the various penetration enhancers shown in Table 9 and 85 parts by weight of the hydrophilic ointment, and tested in the same way as in Example 63.

For comparison, an ointment composed of 5 parts by weight of isosorbide dinitrate and 95 parts by weight of the hydrophilic ointment without the inclusion of the penetration enhancer was tested in the same way as above.

The results are shown in Table 9.

TABLE 9

| | Penetration enhancer | Concentration of isosorbide dinitrate in the blood (ng/ml) | | | | |
|---|---|---|---|---|---|---|
| | | 1 hr. | 3 hrs. | 5 hrs. | 7 hrs. | 24 hrs. |
| Example 64 | Compound (156) | 0.7 | 1.8 | 2.8 | 1.9 | 1.2 |
| Example 65 | Compound (160) | 0.9 | 1.6 | 3.2 | 2.5 | 1.5 |
| Example 66 | Compound (172) | 0.8 | 2.0 | 2.6 | 1.8 | 1.5 |
| Example 67 | Compound (173) | 0.8 | 2.0 | 2.7 | 1.7 | 1.1 |
| Example 68 | Compound (158) | 0.7 | 1.7 | 2.9 | 1.6 | 1.6 |
| Example 69 | Compound (162) | 0.7 | 1.7 | 2.8 | 1.6 | 1.3 |
| Example 70 | Compound (184) | 1.3 | 1.8 | 2.9 | 2.0 | 1.5 |
| Example 71 | Compound (192) | 0.9 | 1.9 | 2.9 | 1.8 | 1.0 |
| Example 72 | Compound (170) | 1.2 | 1.7 | 2.6 | 1.7 | 1.0 |
| Example 73 | Compound (104) | 0.9 | 2.0 | 3.1 | 1.9 | 1.6 |
| Example 74 | Compound (108) | 1.0 | 1.9 | 2.7 | 1.9 | 1.5 |
| Example 75 | Compound (112) | 0.7 | 2.0 | 3.2 | 1.6 | 1.7 |
| Example 76 | Compound (122) | 0.6 | 1.5 | 2.2 | 1.7 | 1.6 |
| Example 77 | Compound (124) | 1.0 | 1.8 | 2.9 | 1.8 | 1.4 |
| Example 78 | Compound (134) | 0.8 | 2.0 | 2.5 | 1.7 | 1.7 |
| Example 79 | Compound (142) | 0.9 | 1.7 | 2.5 | 1.9 | 1.5 |
| Example 80 | Compound (202) | 0.8 | 1.5 | 2.8 | 2.0 | 1.6 |
| Example 81 | Compound (214) | 0.8 | 1.6 | 3.0 | 1.9 | 1.5 |
| Example 82 | Compound (220) | 1.1 | 1.8 | 3.1 | 1.6 | 1.3 |
| Comparison 14 | None | 0.4 | 0.7 | 0.5 | 0.8 | 0.6 |

EXAMPLES 83 AND 84

An ointment composed of 5 parts by weight of nitroglycerin, 10 parts by weight of compound (168) and 85 parts by weight of the hydrophilic ointment, and an ointment composed of 5 parts by weight of nitroglycerin, 10 parts by weight of compound (173) and 85 parts of the hydrophilic ointment were prepared, and tested in the same way as in Example 1.

For comparison, an ointment composed of 5 parts by weight of nitroglycerin and 95 parts by weight of the hydrophilic ointment without the inclusion of the penetration enhancer was prepared and tested in the same way as above.

The results are shown in Table 10.

TABLE 10

| | Ointment composition (wt. %) | | Concentration of nitroglycerin (ng/ml) | |
|---|---|---|---|---|
| | | | 1 hr | 3 hrs |
| Example 83 | Nitroglycerin | 5 | 35 | 40 |
| | Compound (168) | 10 | | |
| | Hydrophilic ointment | 85 | | |
| Example 84 | Nitroglycerin | 5 | 35 | 43 |
| | Compound (173) | 10 | | |
| | Hydrophilic ointment | 85 | | |
| Comparison 15 | Nitroglycerin | 5 | 25 | 29 |
| | Hydrophilic ointment | 95 | | |

EXAMPLES 85 AND 86

Cacao butter (93 parts by weight) and 7 parts by weight of compound (168) or compound (173) were uniformly mixed, and $[Asu^{1.7}]$-eel calcitonin was gradually added and mixed to form a uniform composition. The composition was slightly warmed, and placed into a suppository container to form a suppository for rats having a diameter of about 3 mm and a length of about 6 mm. This suppository contained 0.7 MRC unit of calcitonin. The suppository was intrarectally administered to a rat, and the concentration of calcium in the blood serum after administration was measured by using a calcium measuring kit (made by Iatoron Co.).

For comparison, the same composition as above except that it did not contain compound (168) or compound (173) was prepared and intrarectally administered to a rat, and the calcium concentration in the serum was measured.

The results are shown in Table 11. It is seen that the absorption of calcitonin from the suppository containing the compound (168) or compound (173) was better than that from the comparative suppository.

TABLE 11

| | Suppository composition (wt. %) | | Percent decrease of the serum calcium level from that before administration (%) | | | |
|---|---|---|---|---|---|---|
| | | | 1 hr | 2 hrs | 3 hrs | 5 hrs |
| Example 85 | $[Asu]^{1.7}$-eel calcitonin | 7 | 33.0 | 26.9 | 17.1 | 1.4 |
| | Compound (168) | 7 | | | | |
| | Cacao butter | 93 | | | | |
| Example 86 | $[Asu]^{1.7}$-eel calcitonin | | 31.8 | 25.7 | 18.8 | 1.8 |
| | Compound (173) | 7 | | | | |
| | Cacao butter | 93 | | | | |
| Comparison 16 | $[Asu]^{1.7}$-eel calcitonin | | 3.2 | 1.2 | 0.6 | 0.8 |
| | Cacao butter | | | | | |

EXAMPLES 87 TO 105

Various ointments were prepared from cacao butter, the various penetration enhancers shown in Table 12 and $[Asu^{1.7}]$-eel calcitonin, and tested in the same way as in Example 85.

For comparison, an ointment composed of cacao butter and $[Asu^{1.7}]$-eel calcitonin without the inclusion of the penetration enhancer was prepared and tested in the same way as above.

The results are shown in Table 12.

TABLE 12

| | Penetration enhancer | Percent decrease of the serum calcium level from that before administration (%) | | | |
|---|---|---|---|---|---|
| | | 1 hr. | 2 hrs. | 3 hrs. | 5 hrs. |
| Example 87 | Compound (156) | 31.0 | 27.5 | 18.4 | 2.1 |
| Example 88 | Compound (160) | 36.5 | 28.0 | 15.5 | 1.9 |
| Example 89 | Compound (172) | 32.7 | 30.8 | 20.1 | 1.8 |
| Example 90 | Compound (173) | 30.6 | 30.2 | 14.8 | 2.4 |
| Example 91 | Compound (158) | 28.1 | 29.0 | 15.3 | 1.7 |
| Example 92 | Compound (162) | 31.9 | 29.9 | 19.5 | 1.9 |
| Example 93 | Compound (184) | 29.8 | 25.7 | 14.8 | 3.5 |
| Example 94 | Compound (192) | 30.0 | 31.1 | 16.6 | 2.6 |
| Example 95 | Compound (170) | 29.9 | 30.6 | 17.7 | 2.8 |
| Example 96 | Compound (104) | 30.8 | 28.3 | 20.4 | 3.0 |
| Example 97 | Compound (108) | 30.6 | 27.5 | 15.5 | 2.4 |
| Example 98 | Compound (112) | 31.2 | 29.2 | 21.5 | 2.6 |
| Example 99 | Compound (122) | 31.7 | 26.8 | 17.7 | 2.3 |
| Example 100 | Compound (124) | 33.0 | 30.4 | 16.0 | 1.9 |
| Example 101 | Compound (134) | 31.1 | 30.0 | 14.0 | 2.4 |
| Example 102 | Compound (142) | 32.4 | 28.7 | 15.8 | 2.3 |
| Example 103 | Compound (202) | 35.2 | 25.2 | 13.8 | 2.5 |
| Example 104 | Compound (214) | 33.4 | 28.9 | 17.2 | 1.4 |
| Example 105 | Compound (220) | 20.3 | 34.0 | 18.1 | 1.3 |
| Comparison 17 | None | 3.2 | 1.2 | 0.6 | 0.8 |

EXAMPLES 106 AND 107

Sixty parts by weight of fractionated coconut oil and 10 parts by weight of compound (168) or compound (173) were uniformly mixed, and then hog insulin was gradually added to form a uniform dispersion. The dispersion was filled in a gelatin capsule for suppositories to form a gelatin capsular suppository. These suppository contained 9.6 units of insulin. The suppository was intrarectally administered to a rabbit, and the blood glucose level after administration was measured by the glucose oxidase method.

For comparison, a suppository of the above formulation except that it contained neither the compound (168) nor the compound (173) was prepared, and tested in the same way as above.

The results obtained are shown in Table 13. It is seen that the absorption of insulin from the suppository containing the compound (168) or the compound (173) was better than the comparative suppository.

TABLE 13

| | Suppository composition (wt. %) | | Percent decrease of the blood glucose level from that before the administration (%) | | | |
|---|---|---|---|---|---|---|
| | | | 30 min | 1 hr | 2 hrs | 3 hrs |
| Example 106 | Hog insulin Compound (168) Fractionated coconut oil | 10 90 | 32.8 | 36.3 | 19.1 | 5.2 |
| Example 107 | Hog insulin Compound (173) Fractionated coconut oil | 10 90 | 29.4 | 33.3 | 18.6 | 3.7 |
| Comparison 18 | Hog insulin Fractionated coconut oil | | −3.1 | 0.7 | −1.2 | −1.8 |

EXAMPLE 108

Eighty parts by weight of cacoa butter, 10 parts by weight of compound (168) and 10 parts by weight of cephalothin sodium were uniformly mixed and then slightly warmed. The mixture was filled in a suppository container to form a suppository containing 1 g of the mixture. The suppository was administered intrarectally to a Beagle dog, and the concentration of cephalothin sodium in the blood after administration was measured by the cup method.

For comparison, the same suppository as above except that it did not contain compound (168) was administered intrarectally to a Beagle dog, and the concentration of cephalothin sodium in the blood was measured.

The results obtained are shown in Table 14. It is seen that the absorption of cephalothin sodium from the suppository containing compound (168) was better than that from the comparative suppository.

TABLE 14

| | Suppository composition (wt. %) | | Concentration of cephalothin sodium in the blood (µg/ml) | | | |
|---|---|---|---|---|---|---|
| | | | 1 hr | 3 hrs | 5 hrs | 7 hrs |
| Example 108 | Cephalothin sodium Compound (168) Cacao butter | 10 10 80 | 0.5 | 0.4 | 0.5 | 0.2 |
| Comparison 19 | Cephalothin sodium Cacao butter | 10 90 | 0 | 0 | 0 | 0 |

EXAMPLE 109

Ten parts by weight of compound (168) was mixed uniformly with 90 parts by weight of distilled water, and [Asu$^{1.7}$]-eel caltitonin was gradually added to form a uniform composition as a nasal drop. This nasal drop contained 15 units/50 µl of calcitonin. Fifty microliters of the nasal drop was administered to the nasal cavity of a New Zealand white male rabbit, and the concentration of calcium in the serum after administration was measured by using a calcium measuring kit (made by Iatron Co.).

For comparison, the same composition as above except that it did not contain compound (168) was administered to the nasal cavity of a rabbit, and the concentration of calcium in the serum was measured.

The results are shown in Table 15. It is seen that the absorption of calcitonin from the composition containing compound (168) was better than that from the comparative composition.

TABLE 15

| | Nasal drop | | Percent decrease of the serum calcium level from before administration (%) | | | |
|---|---|---|---|---|---|---|
| | | | 1 hr | 2 hrs | 3 hrs | 5 hrs |
| Example 109 | [Asu$^{1.7}$]-eel calcitonin Compound (168) Distilled water | 10 90 | 6.1 | 4.0 | 1.8 | 0.9 |
| Comparison 20 | [Asu$^{1.7}$[-eel calcitonin Distilled water | 100 | 1.8 | 0.5 | 0.2 | 0 |

EXAMPLES 110 TO 129

A diffusion cell was partitioned by an egg shell membrane. A 1:1 mixture of physiological saline and ethanol containing a drug and compound (168) was filled in the donor side of the cell, and physiological saline, in the acceptor side. While maintaining a temperature of 37° C., the two liquid phases were stirred, and after a lapse of a predetermined period of time, the amount of the drug which diffused into the acceptor side from the donor side was measured.

The diffusion cell used was a glass cell for use in an ordinary diffusion experiment. The egg shell was obtained by removing the contents of an egg from the shell, immersing the shell in 0.7% acetic acid for 30 minutes, subjecting it to ultrasonication for 15 minutes, and carefully peeling the membrane from the shell. The concentration of the drug in the donor side was maintained at 0.05%, and the concentration of compound (168) in the donor side was maintained at 1.0%.

A control test was carried out in the same way as above except that only the drug was added to the donor side.

The amount of the drug which diffused to the acceptor side was measured 30 minutes later, and compared with the control.

The relative amount of the drug diffused from the drug-penetration enhancer system was calculated by taking the amount of the drug diffused from the control donor side as 100. For the above experimental procedure, reference may be had to M. Waslitake et al., Chem. Pharm. Bull., Vol. 20, p. 2855, 1980.

The results are shown in Table 16.

TABLE 16

| Example | Drug on the donor side | Relative amount of the drug diffused (measured 30 minutes later) |
|---|---|---|
| 110 | Cephalothin | 139 |
| 111 | Griseofulvin | 209 |
| 112 | Indomethacin | 217 |
| 113 | Salicylic acid | 203 |
| 114 | Piroxicam | 177 |
| 115 | Triamcinolone acetonide | 214 |
| 116 | 5-Fluorouracil | 208 |
| 117 | Procaine | 149 |
| 118 | Estradiol | 181 |
| 119 | Scopolamine | 116 |
| 120 | p-Aminobenzoic acid | 122 |
| 121 | Bupranolol | 141 |

TABLE 16-continued

| Example | Drug on the donor side | Relative amount of the drug diffused (measured 30 minutes later) |
|---|---|---|
| 122 | Methyldopa | 137 |
| 123 | iso-Sorbitol nitrate | 128 |
| 124 | Diazepam | 144 |
| 125 | Sodium cromoglicate | 159 |
| 126 | Chlorpromazine | 133 |
| 127 | Prostaglandin $F_{2\alpha}$ | 146 |
| 128 | 1,25-Dihydroxyvitamin $D_3$ | 123 |
| 129 | Urokinase | 115 |

EXAMPLE 130

(i) About 10 g of compound (168) was added to 125 g of cacao butter, and they were well mixed by a grinder. Then, 5 g of indomethacin was gradually added and mixed to form a homogeneous composition. The composition was slightly heated to render it flowable, and poured into a container for production of suppositories, followed by solidification at room temperature to obtain solid suppositories for human application each having a weight of 1.4 g. One suppository contained about 0.05 g of indomethacin.

(ii) About 5 g of compound (168) was dispersed in 35 g of fractionated coconut oil, and 100 of cefaloridine was added, and well stirred in a mixer to obtain a homogeneous dispersion. 500 mg of the dispersion was filled into a gelatin capsule for suppositories to obtain gelatin capusule suppositories for humans. One capsule contained about 500 ml of cefaloridine.

EXAMPLE 131

One gram of beclomethasone dipropionate and 5 g of compound (168) were added to 1,000 g of hydroxypropyl cellulose. They were mechanically mixed to form a powder having beclomethasone dipropionate uniformed dispersed therein. Fifty milligrams of the powder was filled in a #2 hard gelatin capsule to form a powdery preparation for nasal administration in unit dosage form.

EXAMPLE 132

Fifty parts by weight of white beeswax was melted by heating, and 0.02 part by weight of $l\alpha$-hydroxycholecalciferol and compound (168) were added. The mixture was well stirred. After it became uniform, 50 parts of purified lanolin and 880 parts by weight of white Vaseline were added, and the mixture was stirred. When the entire mixture became a uniform liquid, the heating was stopped, and the stirring was continued until it became solid. Thus, an ointment was obtained.

EXAMPLE 133

An ointment for administration to the oral cavity was prepared from 2 parts by weight of compound (168), 2.5 parts by weight of polyethylene (molecular weight about 20,000), 45.5 parts by weight of liquid paraffin, 16.5 parts by weight of gelatin, 165 parts by weight of pectin, 17 parts by weight of carboxymethyl cellulose sodium and 0.1 part by weight of triamcinolone acetonide.

EXAMPLE 134

One part by weight of fluocinolone, 15 parts by weight of cetyl alcohol, 10 parts by weight of propylene glycol, 15 parts by weight of sodium laurylsulfate, 2 parts by weight of compound (168) and 30 parts by weight of water were mixed under heat until the mixture became uniform. Then, the heating was stopped, and the mixture was left to stand. When its temperature returned to room temperature, 25 parts by weight of water was added, and the mixture was stirred until it became uniform. Thus, a lotion was prepared.

EXAMPLE 135

A cream was prepared from 1 part by weight of griseofulvin, 12 parts by weight of stearyl alcohol, 0.5 part by weight of cholesterol, 8 parts by weight of white beeswax, 1 part by weight of sorbitan monoleate, 3 parts by weight of Polysorbate 80, 2 parts by weight of compound (168), 1 part by weight of sorbitol, 0.5 part by weight of sodium tartrate and 71 parts by weight of purified water.

EXAMPLE 136

Safety of the penetration enhancer of the invention:

0.05 ml of a 0.8% or 2.4% aqueous solution of each of the penetration enhancers of this invention shown in Table 17 was applied dropwise to one eye of white native male rabbits (body weight 2.0 to 3.0 kg; 3 per group) which, it had been ascertained, were free from any trouble at the cornea, iris and conjunctiva. Nothing was applied to the other eye. Thus, irritation of the absorption aid to the mucous membrane of the eyes were examined, and scores were calculated in accordance with the Draize's eye irritation evaluating method [Association of Foods, "Drugs and Cosmetics" (1957)]. The results are shown in Table 17.

As a control, sodium laurylsulfate, a kind of surface-active agent, was evaluated in the same way, and the results are also shown in Table 17.

The results demonstrate that the penetration enhancers used in this invention, show almost no irritation, but sodium layrylsulfate used as a control exhibit fairly strong irritation.

TABLE 17

| | | Primary irritation scores on the eyes | | | | | | | |
|---|---|---|---|---|---|---|---|---|---|
| | | Hours after application | | | | | | | |
| (W/v% soln) | Site | 1 | 3 | 6 | 24 | 48 | 72 | 96 | 168 |
| Compound (172) | Cornea | 0 | 0 | 0 | 0 | 0 | 0 | 0 | 0 |
| 2.4% | Iris | 0 | 0 | 0 | 0 | 0 | 0 | 0 | 0 |
| | Conjunctiva | 3.3 | 2.0 | 1.3 | 0 | 0 | 0 | 0 | 0 |
| | Total | 3.3 | 2.0 | 1.3 | 0 | 0 | 0 | 0 | 0 |
| Compound (162) | Cornea | 0 | 0 | 0 | 0 | 0 | 0 | 0 | 0 |
| 2.4% | Iris | 0 | 0 | 0 | 0 | 0 | 0 | 0 | 0 |
| | Conjunctiva | 3.3 | 2.0 | 2.0 | 0 | 0 | 0 | 0 | 0 |
| | Total | 3.3 | 2.0 | 2.0 | 0 | 0 | 0 | 0 | 0 |
| Compound (168) | Cornea | 0 | 0 | 0 | 0 | 0 | 0 | 0 | 0 |
| 2.4% | Iris | 0 | 0 | 0 | 0 | 0 | 0 | 0 | 0 |
| | Conjunctiva | 2.0 | 2.0 | 1.3 | 0 | 0 | 0 | 0 | 0 |

TABLE 17-continued

| (W/v% soln) | Site | Primary irritation scores on the eyes Hours after application | | | | | | | |
|---|---|---|---|---|---|---|---|---|---|
| | | 1 | 3 | 6 | 24 | 48 | 72 | 96 | 168 |
| | Total | 2.0 | 2.0 | 1.3 | 0 | 0 | 0 | 0 | 0 |
| Compound (108) | Cornea | 0 | 0 | 0 | 0 | 0 | 0 | 0 | 0 |
| 0.8% | Iris | 0 | 0 | 0 | 0 | 0 | 0 | 0 | 0 |
| | Conjunctiva | 2.0 | 2.0 | 1.3 | 0 | 0 | 0 | 0 | 0 |
| | Total | 2.0 | 2.0 | 1.3 | 0 | 0 | 0 | 0 | 0 |
| Compound (134) | Cornea | 0 | 0 | 0 | 0 | 0 | 0 | 0 | 0 |
| 2.4% | Iris | 0 | 0 | 0 | 0 | 0 | 0 | 0 | 0 |
| | Conjunctiva | 3.3 | 1.3 | 1.3 | 0 | 0 | 0 | 0 | 0 |
| | Total | 3.3 | 1.3 | 1.3 | 0 | 0 | 0 | 0 | 0 |
| Compound (214) | Cornea | 0 | 0 | 0 | 0 | 0 | 0 | 0 | 0 |
| 2.4% | Iris | 0 | 0 | 0 | 0 | 0 | 0 | 0 | 0 |
| | Conjunctiva | 2.0 | 2.0 | 2.0 | 0 | 0 | 0 | 0 | 0 |
| | Total | 2.0 | 2.0 | 2.0 | 0 | 0 | 0 | 0 | 0 |
| Sodium | Cornea | 0 | 0 | 0 | 0 | 0 | 0 | 0 | 0 |
| Laurylsulfate | Iris | 0 | 0 | 0 | 0 | 0 | 0 | 0 | 0 |
| 0.1% | Conjunctiva | 4.0 | 4.0 | 0 | 0 | 0 | 0 | 0 | 0 |
| | Total | 4.0 | 4.0 | 0 | 0 | 0 | 0 | 0 | 0 |
| Sodium | Cornea | 0 | 0 | 0 | 0 | 0 | 0 | 0 | 0 |
| Laurylsulfate | Iris | 5.0 | 0 | 0 | 0 | 0 | 0 | 0 | 0 |
| 2.4% | Conjunctiva | 13.3 | 12.7 | 11.3 | 8.0 | 4.0 | 2.7 | 2.0 | 0.7 |
| | Total | 18.3 | 12.7 | 11.3 | 8.0 | 4.0 | 2.7 | 2.0 | 0.7 |

Note:
The scores are averages for three rabbits.

What is claimed is:

1. A method for administering a pharmacologically active agent to a warm-blooded animal, which comprises externally applying (A) a pharmaceutically effective amount of the pharmacologically active agent selected from the group consisting of an anti-inflammatory agent, an agent for the circulatory system, an anti-ulcer agent, a hormone, an agent for the respiratory system, an agent for the central nervous system, a biological material and an agent for the metabolic system, in combination with (B) a penetration enhancer of the following formula (I)

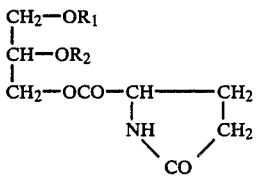

wherein $R_1$ and $R_2$ are identical or different and each represents a hydrogen atom, an alkyl group having 1 to 25 carbon atoms, an alkenyl group having 2 to 25 carbon atoms, a ($C_{1-24}$ alkyl)carbonyl group or a ($C_{2-24}$ alkenyl)carbonyl group, provided that $R_1$ and $R_2$ are not hydrogen atoms at the same time, or $R_1$ and $R_2$, taken together, may form a group of the following formula (a)

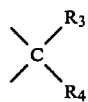

in which $R_3$ and $R_4$ are identical or different and each represents a hydrogen atom, an alkyl group having 1 to 24 carbon atoms or an alkenyl group having 2 to 24 carbon atoms, to the surface of the skin or mucosa of the warm-blooded animal to enhance the penetration of a pharmaceutically effective amount of the pharmacologically active agent through the skin or mucosa.

2. The method of claim 1 wherein the pharmacologically active agent (A) is applied together with the penetration enhancer (B) to the surface of the skin of the warm-blooded animal.

3. The method of claim 2 wherein the pharmacologically active agent (A) and the penetration enhancer (B) are applied as a composition comprising them.

4. The method of claim 1 wherein the pharmacologically active agent (A) is applied together with the penetration enhancer (B) to the surface of the rectal mucosa of the warm-blooded animal.

5. The method of claim 4 wherein the pharmacologically active agent (A) and the penetration enhancer (B) are applied as a composition comprising them.

6. The method of claim 1 wherein the pharmacologically active agent (A) is applied together with the penetration enhancer (B) to the surface of the mucosa of the oral cavity of the warm-blooded animal.

7. The method of claim 6 wherein the pharmacologically active agent (A) and the penetration enhancer (B) are applied as a composition comprising them.

8. The method of claim 1 wherein the pharmacologically active agent (A) is applied together with the penetration enhancer (B) to the surface of the mucosa of the nasal cavity of the warm-blooded animal.

9. The method of claim 8 wherein the pharmacologically active agent (A) and the penetration enhancer (B) are applied as a composition comprising them.

10. The method of claim 1 wherein the pharmacologically active agent (A) and the penetration enhancer (B) are applied as a composition comprising them.

* * * * *